(12) United States Patent
Peyman

(10) Patent No.: US 9,216,067 B2
(45) Date of Patent: Dec. 22, 2015

(54) VITREOUS CUTTER SLEEVE AND A VITREOUS CUTTER SYSTEM USING THE SAME

(71) Applicant: Gholam A. Peyman, Sun City, AZ (US)

(72) Inventor: Gholam A. Peyman, Sun City, AZ (US)

( * ) Notice: Subject to any disclaimer, the term of this patent is extended or adjusted under 35 U.S.C. 154(b) by 0 days.

(21) Appl. No.: 14/622,862

(22) Filed: Feb. 14, 2015

(65) Prior Publication Data

US 2015/0157415 A1  Jun. 11, 2015

Related U.S. Application Data

(63) Continuation-in-part of application No. 13/242,323, filed on Sep. 23, 2011, now Pat. No. 8,979,867.

(51) Int. Cl.
| | | |
|---|---|---|
| *A61B 19/00* | (2006.01) | |
| *A61B 17/32* | (2006.01) | |
| *A61F 9/007* | (2006.01) | |
| *A61F 9/008* | (2006.01) | |

(52) U.S. Cl.
CPC .............. *A61B 19/5202* (2013.01); *A61B 17/32* (2013.01); *A61F 9/00736* (2013.01); *A61F 9/00821* (2013.01); *A61B 2217/005* (2013.01); *A61F 2009/00874* (2013.01)

(58) Field of Classification Search
CPC .............. A61B 17/32; A61B 17/3421; A61B 19/5202; A61B 2217/005; A61F 9/00736
See application file for complete search history.

(56) References Cited

U.S. PATENT DOCUMENTS

| | | | |
|---|---|---|---|
| 4,019,514 A | | 4/1977 | Banko |
| 4,099,529 A | | 7/1978 | Peyman |
| 4,551,129 A | | 11/1985 | Coleman et al. |
| 4,841,984 A | * | 6/1989 | Armeniades et al. .......... 600/561 |
| 5,591,160 A | * | 1/1997 | Reynard ........................... 606/15 |
| 5,690,663 A | | 11/1997 | Stephens |
| 5,725,514 A | | 3/1998 | Grinblat et al. |
| 6,066,138 A | * | 5/2000 | Sheffer et al. ..................... 606/49 |
| 6,936,053 B1 | * | 8/2005 | Weiss ............................. 606/107 |
| 7,783,346 B2 | * | 8/2010 | Smith et al. ...................... 604/21 |
| 8,231,544 B2 | * | 7/2012 | Mark ............................. 600/566 |

(Continued)

OTHER PUBLICATIONS

First office action on the merits (Non-Final Rejection) in U.S. Appl. No. 13/242,323, sent on Jul. 13, 2012.

(Continued)

*Primary Examiner* — Thomas McEvoy
*Assistant Examiner* — Julie A Szpira
(74) *Attorney, Agent, or Firm* — The Law Office of Patrick F. O'Reilly III, LLC

(57) ABSTRACT

A vitreous cutter sleeve is disclosed herein. The vitreous cutter sleeve includes an elongate tubular body with a peripheral sidewall and a central passageway disposed through the elongate tubular body, the central passageway of the elongate tubular body configured to receive a vitreous cutter therein, at least a portion of the elongate tubular body being formed from a material that is transparent to visible light, the material being further configured to conduct at least one of infrared radiation, radiofrequency radiation, and an electrical current; and an illumination device operatively coupled to the elongate tubular body such that the illumination device is capable of providing illumination to an inside portion of an eye through at least a portion of the peripheral sidewall of the elongate tubular body. A vitreous cutter system that includes a vitreous cutter and a vitreous cutter sleeve is also disclosed herein.

19 Claims, 10 Drawing Sheets

(56) References Cited

U.S. PATENT DOCUMENTS

| | | | |
|---|---|---|---|
| 2005/0135776 A1* | 6/2005 | Vijfvinkel | 385/147 |
| 2007/0197856 A1* | 8/2007 | Gellman et al. | 600/16 |
| 2007/0225727 A1 | 9/2007 | Matsuhisa et al. | |
| 2008/0086160 A1 | 4/2008 | Mastri et al. | |
| 2008/0312662 A1* | 12/2008 | Hickingbotham | 606/107 |
| 2011/0112377 A1* | 5/2011 | Papac et al. | 600/249 |
| 2011/0230728 A1 | 9/2011 | Artsyukhovich et al. | |
| 2012/0035425 A1* | 2/2012 | Schaller | 600/249 |
| 2012/0083793 A1 | 4/2012 | Foster | |
| 2013/0079806 A1 | 3/2013 | Peyman | |

OTHER PUBLICATIONS

Second office action on the merits (Final Rejection) in U.S. Appl. No. 13/242,323, sent on Jun. 6, 2013.

Third office action on the merits (Non-Final Rejection) in U.S. Appl. No. 13/242,323, mailed on Apr. 14, 2014.

Notice of Allowance in U.S. Appl. No. 13/242,323, mailed on Nov. 6, 2014.

* cited by examiner

SECTION A-A

SECTION B-B

Detail "A"

Detail "B"

VITREOUS CUTTER SLEEVE AND A VITREOUS CUTTER SYSTEM USING THE SAME

CROSS-REFERENCE TO RELATED APPLICATIONS

This patent application is a continuation-in-part application of U.S. Non-Provisional patent application Ser. No. 13/242,323, entitled "VITREOUS CUTTER", filed on Sep. 23, 2011, which is incorporated by reference herein in its entirety by this reference thereto.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The present invention is related to vitreous cutters and sleeves that are used in vitrectomy procedures to remove vitreous from the eye. In particular, the present invention is related to vitreous cutters and sleeves having a light source to illuminate a portion of the eye.

2. Background and Description of Related Art

Vitrectomy is a procedure in which the degenerative vitreous is removed to clear the opaque optical media (vitreous) or to eliminate traction on the retina which produces a localized or generalized retinal detachment. The function of a vitrectomy instrument is described in U.S. Pat. No. 4,099,529 to Peyman, the entire contents of which are herein incorporated by reference. That is, generally, the cutting part includes concentric tubing. An inner tube serves as the inner cutting edge of the instrument and has an oscillating action, and the opening in the tightly fit outer tube serves as the outer edge of the cutting. The vitreous is aspirated through a small opening close to the tip of the outer stationary tube, i.e., the outer cutting edge. The aspiration force, generated by a pump, when applied through the inner tube draws the vitreous through the outer hole toward the inside of the inner tube. The oscillation of the inner tube cuts the vitreous/tissue trapped in the opening of the outer tube and is aspirated into a reservoir. To balance the intraocular pressure, physiologic saline solution is infused through a second independent "infusion tube" placed inside the eye cavity through a separate incision in the eye wall.

During the procedure, the vitreous cavity is illuminated through a separate fiber optic brought inside the eye through a third incision. The diameter of the vitrectomy cutting cutters varies between 20-23-25-27 gauge. The most desirous sizes are 23 gauge, 25 gauge, and 27 gauge tubes because these sizes eliminate the need to close the incision in the eye wall by a suture and the smaller the instrument is, the less traumatic the surgery becomes.

There are several disadvantages of the conventional systems. First, there is a need for at least three incisions for the cutter, infusion and the light sources. Second, the 25 gauge and 27 gauge tips, because of their size are too flexible inside the eye. That is, the slightest pressure that moves the eye during surgery also can bend the shaft of the cutter in one direction at the incision site while the inside portion of the shaft moves in another direction. This movement can be disturbing to an operator who does not expect motion in the opposite direction than that which was intended and can cause injury to the fine structure of the lens or the retina. Third, in myopic eyes having a longer axial length than normal, a longer (36-38 mm) than normal shaft (e.g., 30 mm) is required. This makes the instrument flimsy and not desirable.

In addition, in conventional systems, the tip of the vitrectomy instrument, which often contacts a contaminated portion of the eye, such as a tumor, may spread contaminated and cancerous tissue to other healthy portions of the eye. As such, what is needed is a device for containing the contaminated tip of the vitrectomy instrument after it is used to penetrate contaminated tissue of the eye so that any residual contaminated tissue present on the tip of the vitrectomy cutter is not spread to other, healthy portions of the eye as the vitrectomy instrument is being removed from the eye at the conclusion of the procedure. In addition, there is a need for the device, which contains the contaminated tip of the vitrectomy instrument, to incorporate other integral features that facilitate the performance of the procedure on eye.

BRIEF SUMMARY OF EMBODIMENTS OF THE INVENTION

Accordingly, the present invention is directed to a vitreous cutter sleeve and a vitreous cutter system using the same that substantially obviates one or more problems resulting from the limitations and deficiencies of the related art.

In accordance with one or more embodiments of the present invention, there is provided a vitreous cutter sleeve that includes an elongate tubular body having a first end and a second end disposed opposite to the first end, the elongate tubular body including a peripheral sidewall and a central passageway disposed through the elongate tubular body, the central passageway of the elongate tubular body configured to receive a vitreous cutter therein, at least a portion of the elongate tubular body being formed from a material that is transparent to visible light, the material being further configured to conduct at least one of infrared radiation, radiofrequency radiation, and an electrical current; and an illumination device operatively coupled to the elongate tubular body such that the illumination device is capable of providing illumination to an inside portion of an eye through at least a portion of the peripheral sidewall of the elongate tubular body.

In a further embodiment of the present invention, the illumination device is in the form of a fiber optic; and wherein the first end of the elongate tubular body comprises a connector member for connecting the fiber optic to the elongate tubular body of the vitreous cutter sleeve so that light is capable of being transmitted from the fiber optic to an interior of the peripheral sidewall of the elongate tubular body, the connector member being disposed on a portion of the elongate tubular body that does not enter the eye.

In yet a further embodiment, at least one of following devices is operatively coupled to the vitreous cutter sleeve: (i) a laser generation device for generating electromagnetic radiation ranging from blue light to infrared radiation, inclusive, (ii) a radiofrequency generation device for generating radiofrequency radiation, and (iii) an electrocautery device for generating an electrical current that is capable of cauterizing tissue of the eye.

In still a further embodiment, the first end of the elongate tubular body comprises a flared end portion configured to prevent the vitreous cutter sleeve from entering too deep into the eye, and wherein the vitreous cutter sleeve further includes a pierceable membrane disposed within the central passageway of the elongate tubular body proximate to the first end, the pierceable membrane configured to create a substantially liquid-tight seal between an outer peripheral surface of the vitreous cutter and an inner peripheral surface of the peripheral sidewall of the vitreous cutter sleeve after the vitreous cutter has penetrated the pierceable membrane.

In yet a further embodiment, the second end of the elongate tubular body comprises a pointed tip configured to cut through tissue of the eye.

In still a further embodiment, the elongate tubular body comprises a plurality of opaque band portions spaced apart along a length thereof, each of the plurality of opaque bands portions being spaced apart from one another by a respective one of a plurality of transparent band portions, each of the plurality of transparent band portions being transparent to visible light.

In yet a further embodiment, each of the plurality of opaque band portions are spaced apart from one another by a substantially constant distance such that the plurality of opaque bands portions and the plurality of transparent band portions are capable of being used to determine a depth of insertion of the vitreous cutter sleeve into tissue of the eye.

In still a further embodiment, the plurality of opaque band portions of the elongate tubular body are formed by coating the peripheral sidewall of the elongate tubular body with a black material.

In yet a further embodiment, the elongate tubular body comprises an opaque coating from the first end to an exposed tip at the second end so as to enable the exposed tip to function as a localized light source.

In still a further embodiment, the material is transparent to visible light from 400-800 nm, and wherein the material comprises one of: (i) metal glass, (ii) amorphous glass, (iii) palladium alloy, (iv) zirconium alloy, and (v) aluminum nitryloxyde.

In yet a further embodiment, the elongate tubular body comprises insulation from the first end to an exposed tip at the second end so as to enable the exposed tip to function as a localized cauterizer.

In accordance with one or more other embodiments of the present invention, there is provided a vitreous cutter sleeve that includes an elongate tubular body having a first end and a second end disposed opposite to the first end, the elongate tubular body including a peripheral sidewall and a central passageway disposed through the elongate tubular body, the central passageway of the elongate tubular body configured to receive a vitreous cutter therein, at least a portion of the elongate tubular body being formed from a material that is transparent to visible light, the material being further configured to conduct at least one of infrared radiation, radiofrequency radiation, and an electrical current, the first end of the elongate tubular body comprising a flared end portion configured to prevent the vitreous cutter sleeve from entering too deep into the eye, and the second end of the elongate tubular body comprising a pointed tip configured to cut through tissue of the eye; and an illumination device operatively coupled to the elongate tubular body such that the illumination device is capable of providing illumination to an inside portion of an eye through at least a portion of the peripheral sidewall of the elongate tubular body.

In a further embodiment of the present invention, the elongate tubular body comprises a plurality of opaque band portions spaced apart along a length thereof, each of the plurality of opaque bands portions being spaced apart from one another by a respective one of a plurality of transparent band portions, each of the plurality of transparent band portions being transparent to visible light.

In yet a further embodiment, each of the plurality of opaque band portions are spaced apart from one another by a substantially constant distance such that the plurality of opaque bands portions and the plurality of transparent band portions are capable of being used to determine a depth of insertion of the vitreous cutter sleeve into tissue of the eye.

In still a further embodiment, at least one of following devices is operatively coupled to the vitreous cutter sleeve: (i) a laser generation device for generating electromagnetic radiation ranging from blue light to infrared radiation, inclusive, (ii) a radiofrequency generation device for generating radiofrequency radiation, and (iii) an electrocautery device for generating an electrical current that is capable of cauterizing tissue of the eye.

In accordance with yet one or more other embodiments of the present invention, there is provided a vitreous cutter system comprising a vitreous cutter and a vitreous cutter sleeve. The vitreous cutter includes an elongate outer tube with a body having a closed end tip, the body of the elongate outer tube including a sidewall extending in axial direction from the closed end tip, the body of the elongate outer tube defining a linear passageway closed at a distal end by the closed end tip, the elongate outer tube further including an opening disposed in the sidewall of the body, the opening being disposed proximate to the closed end tip of the body, and the opening being configured to enable cutting of vitreous or tissue; and an elongate inner tube arranged concentrically within the elongate outer tube, the elongate inner tube being configured to oscillate so as to be capable of cutting the vitreous or the tissue that enters the opening in the body of the elongate outer tube. The vitreous cutter sleeve includes an elongate tubular body having a first end and a second end disposed opposite to the first end, the elongate tubular body including a peripheral sidewall and a central passageway disposed through the elongate tubular body, the central passageway of the elongate tubular body slidingly receiving the vitreous cutter therein, at least a portion of the elongate tubular body being formed from a material that is transparent to visible light, the material being further configured to conduct at least one of infrared radiation, radiofrequency radiation, and an electrical current; and an illumination device operatively coupled to the elongate tubular body such that the illumination device is capable of providing illumination to an inside portion of an eye through at least a portion of the peripheral sidewall of the elongate tubular body.

In a further embodiment of the present invention, the elongate inner tube of the vitreous cutter is configured to remove the cut vitreous or the cut tissue by the vitreous cutter applying an aspiration force to the cut vitreous or the cut tissue.

In yet a further embodiment, the aspiration force applied by the vitreous cutter is configured to draw the cut vitreous or the cut tissue through the opening disposed in the sidewall of the body of the elongate outer tube.

In still a further embodiment, the vitreous cutter sleeve is configured to contain the closed end tip of the vitreous cutter when the vitreous cutter is being removed from the eye so as to prevent the closed end tip from contacting and contaminating healthy tissue in the eye.

In yet a further embodiment, the elongate tubular body comprises a plurality of opaque band portions spaced apart along a length thereof, each of the plurality of opaque bands portions being spaced apart from one another by a respective one of a plurality of transparent band portions, each of the plurality of transparent band portions being transparent to visible light. Each of the plurality of opaque band portions are spaced apart from one another by a substantially constant distance such that the plurality of opaque bands portions and the plurality of transparent band portions are capable of being used to determine a depth of insertion of the vitreous cutter sleeve into tissue of the eye.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

An object of one or more embodiments of the present invention is to provide vitrectomy cutters 1) with harder than stainless steel material that eliminate the short coming of the vitreous cutters; 2) that eliminate the need for additional incisions made for the fiber optic illumination by bringing the light through the shaft of the cutter; 3) that can be used as a needle for penetrating the tissue as a biopsy probe; and 4) one could have a combination of a probe for cutting, illumination and infusion in a single instrument that would have a 23-25 gauge diameter, and would not require an additional incision or suturing the entrance wound. This modification would eliminate all of the above-described shortcomings of the conventional systems and would also provide an instrument with a longer shaft of up to 38 mm long or longer.

Figure 1:
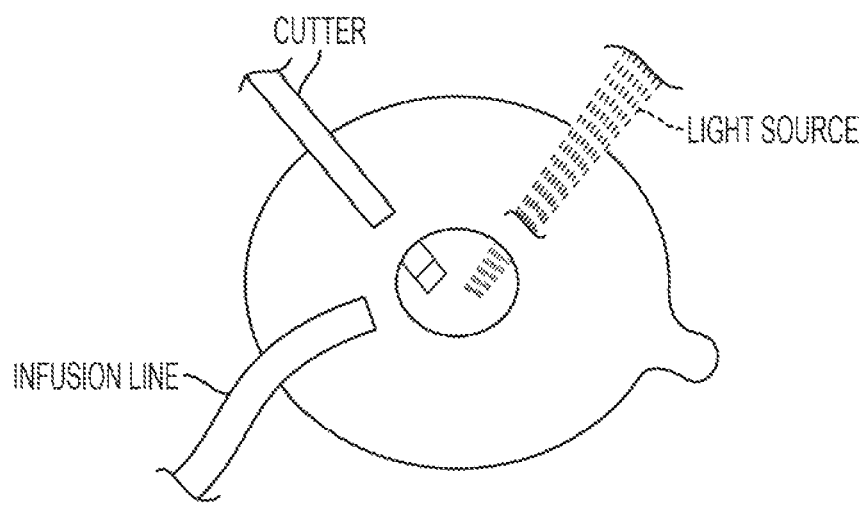
FIG. 1 illustrates a conventional vitrectomy that requires three independent incisions of different sizes for the three instruments (cutter, infusion, illumination)
Figure 2:
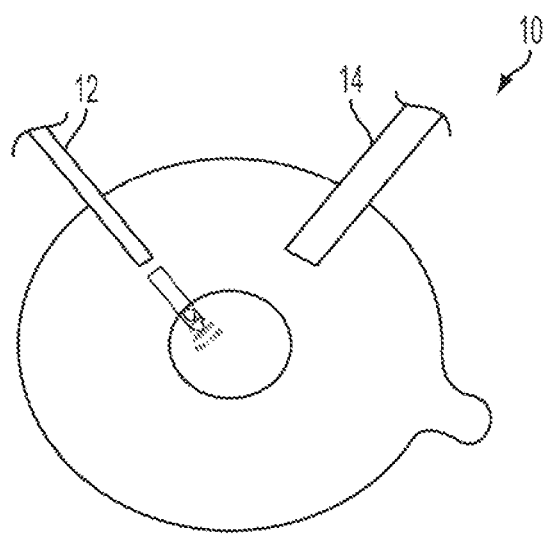
FIG. 2 illustrates an embodiment of the present invention having three functions using two small sized cutters, 20-30 gauge.
Figure 3A:
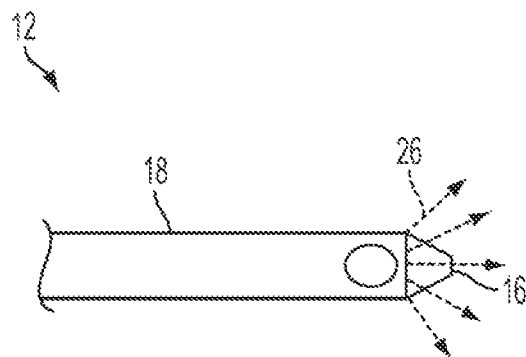
FIGS. 3A and 3B show embodiments of the present invention having a modified tip for the cutter for penetration in the tissue (FIG. 3A having illumination and FIG. 3B without illumination)
Figure 3B:
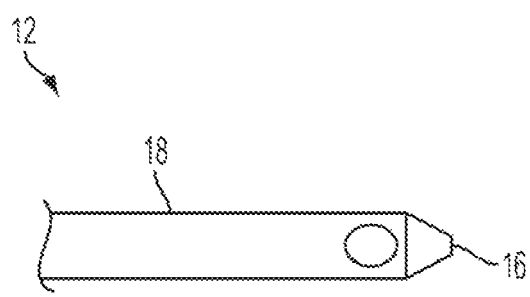
Figure 4A:
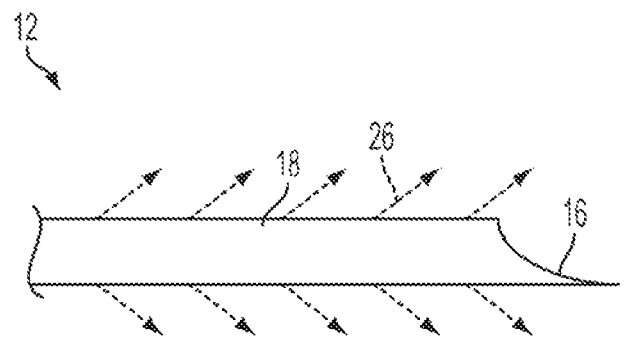
FIG. 4A illustrates an embodiment of the present invention in which the needle for the cutter is illuminated and is uncoated.
Figure 4B:
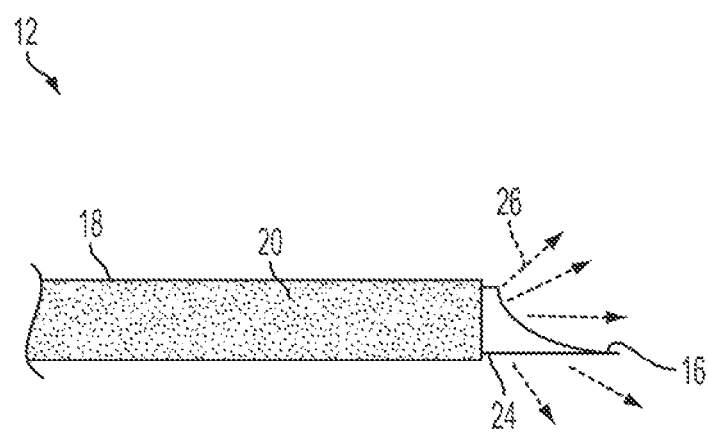
FIG. 4B illustrates an embodiment of the present invention in which the needle for the cutter is illuminated and is partially coated, so that light only generally shines through the tip.
Figure 5:
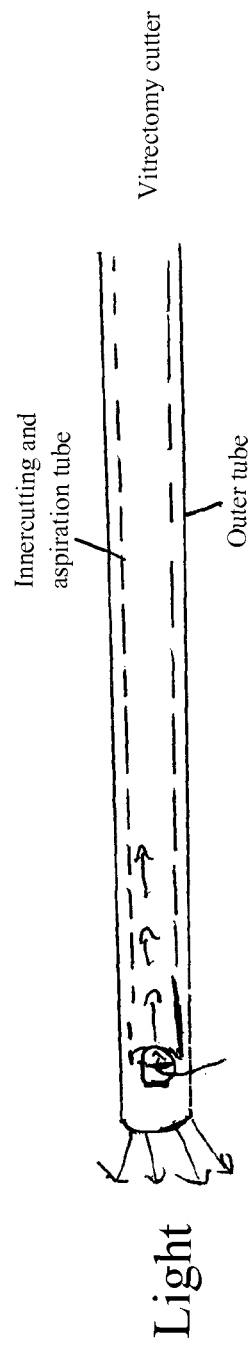
FIG. 5 illustrates a vitreous cutter including two tubes, according to an embodiment of the present invention.

It is a further object of one or more embodiments to create a 30 gauge cutter made of two concentric tubes. The outer tube has an opening in its distal end of its body through which vitreous or tissue is aspirated inside the inner tube (see FIG. 5). The inner tube simultaneously has an oscillating and cutting action. The cut and aspirated matter is removed through the inner tube connected with a vacuum system. These and other embodiments can be used also for obtaining tissue biopsy from not only the intraocular tumors but other tumors such as breast, prostate etc.

In one or more embodiments, these objects may be accomplished by a vitrectomy cutter including a needle with a body and a tip, the needle being made from one of metal glass and amorphous glass, and an illumination device disposed inside the needle body, such that the illumination device is capable of providing illumination to an entire portion of the eye through at least one of the tip of the needle and the body of the needle.

As shown in FIGS. 2-4B, an illustrative vitrectomy method uses a system 10 that includes a cutter device or instrument 12 with illumination and an infusion line 14. The instrument 12 includes a tip 16 and body 18. Such a system enables fewer incisions to be made in the eye, relative to conventional systems. In one embodiment, the tip 16 of the cutter device 12 can be made to be like standard needles used for vein puncture to draw blood from a subject. In another embodiment, a simple needle can be created with these characteristics for infusion or drawing blood from a subject.

The instrument can be illuminated by any standard illuminating system providing the needed light intensity. The illumination device can be disposed inside or outside the needle or in any suitable position relative to the needle. The illumination device is preferably connected to the needle/cutter at a site that does not enter the body. It can either illuminate the entire needle/cutter or the outer surface of the instrument can be coated with a thin layer of black material 20 (see FIG. 4B) leaving only the tip 16 or an area 24 adjacent the tip free to permit the light 26 to exit the instrument. The illumination permits visualization of the tissue, once the needle has penetrated a soft tissue and can be followed by observing its path and position of the needle tip. This eliminates guessing how far a needle has penetrated the tissue.

It is to be understood that the tip of the instrument can be made with any desired shape, which includes round, pointed, sharp blade, etc. or any length.

The cutter 12 can be made from various composites such as metal glass, amorphous glass or similar alloys such as palladium alloy and zirconium alloy, or any other suitable material. These compounds are tougher than presently used stainless steel for conventional vitrectomy cutters or needles. These compounds are also transparent to visible light from 400-800 nanometers (nm), such that it is possible to direct the light for visualization through the body of the cutter without increasing the diameter of the instrument or the need for additional incision for a fiber optic. Similarly, aluminum nitryloxyde is a transparent polycrystalline ceramic structure composed of aluminum and oxygen. This compound is harder than fused silica glass and sapphire or magnesium aluminum. It is light weight and resistant to damage by oxidation or radiation. The manufacturing technique is known and is as with conventional ceramic powder.

In one or more embodiments, the vitreous cutter or needle 12 is made of a hard resistance metal glass alloy. The wall of the outer tubing or the entire needle may be illuminated when connected to a light source. The instrument, when inserted inside the tissue or the eye, provides illumination, thereby illuminating the surrounding tissue structure and eliminating the need for additional internal or external illumination.

It should be understood that the invention is not limited to the above-described materials, but rather, other suitable compounds that can provide the hardness and light transparency, and are not brittle, may be used.

Now, with reference to FIGS. 6 and 7, a first illustrative embodiment of a vitreous cutter sleeve 30 will be described. As shown in these figures, the vitreous cutter sleeve 30 includes an elongate tubular body 32 having a first end 32a and a second end 32b disposed opposite to the first end 32a. The elongate tubular body 32 further includes a peripheral sidewall (i.e., the tubular sidewall in FIG. 6) and a central cylindrical passageway 33 disposed through the elongate tubular body 32. The central cylindrical passageway 33 of the elongate tubular body 32 is configured to receive a vitreous cutter therein (e.g., as shown in FIG. 8), and at least a portion of the elongate tubular body 32 is formed from a material that is transparent to visible light (as will be described in more detail hereinafter). The material forming the elongate tubular body 32 of the sleeve 30 may be further configured to conduct at least one of infrared radiation, radiofrequency radiation, and an electrical current. Referring again to FIGS. 6 and 7, it can be seen that the vitreous cutter sleeve 30 further includes an illumination device (e.g., fiber optic 40) operatively coupled to the elongate tubular body 32 via a light-transmitting connector member 42 so that the illumination device 40 is capable of providing illumination to an inside portion of an eye through at least a portion of the peripheral sidewall of the elongate tubular body 32 (i.e., through the transparent bands 38 in FIG. 6).

Figure 6:
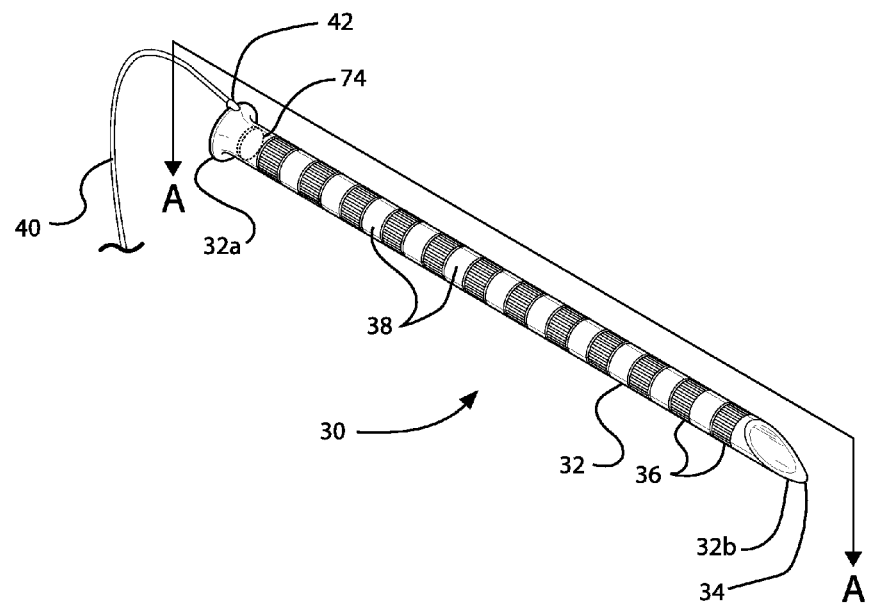
FIG. 6 illustrates a vitreous cutter sleeve, according to one embodiment of the present invention, wherein the body of the vitreous cutter sleeve is provided with a plurality of opaque bands spaced-apart along the length thereof, and a plurality of transparent bands disposed between the opaque bands.
Figure 7:
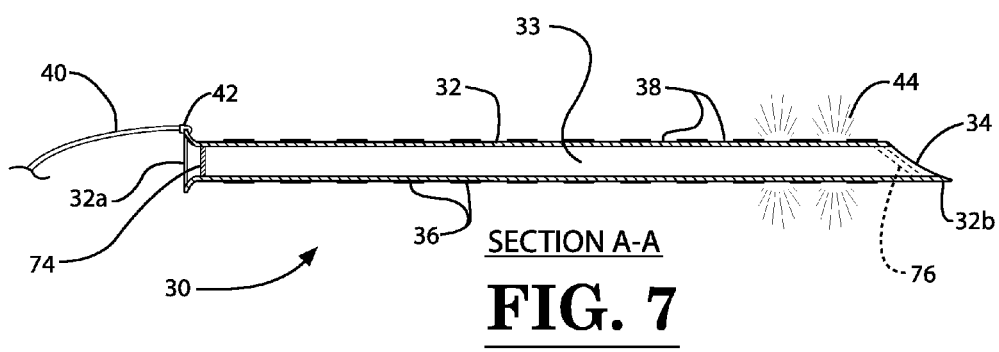
FIG. 7 is a longitudinal sectional view of the vitreous cutter sleeve of FIG. 6, wherein the section is generally cut along the cutting-plane line A-A in FIG. 6.
Figure 8:
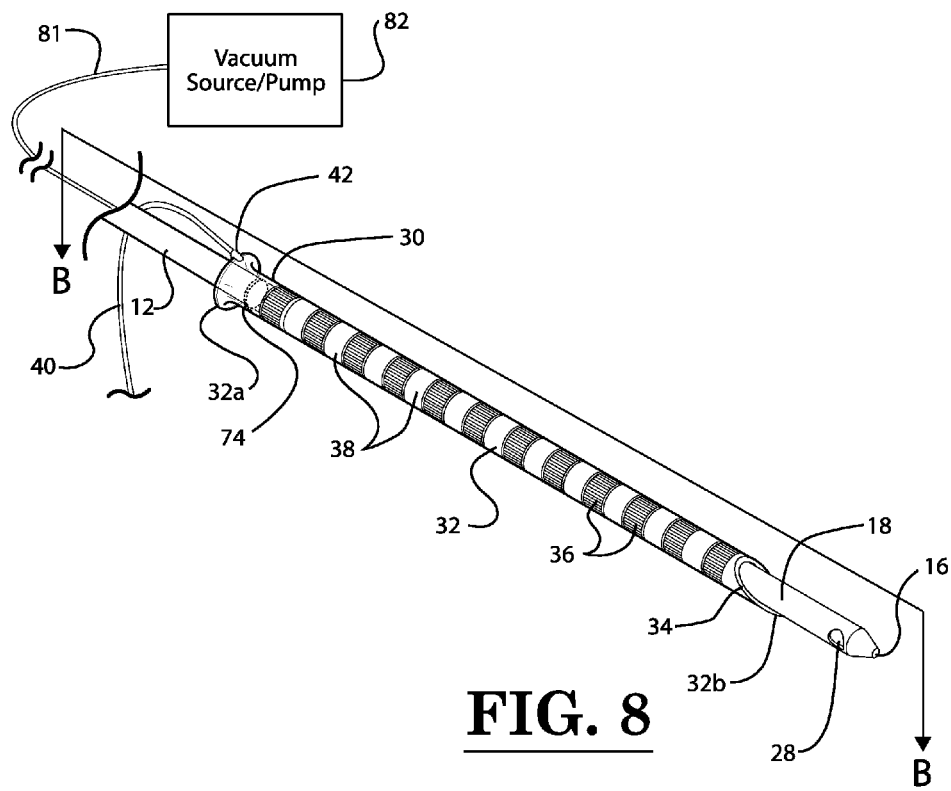
FIG. 8 illustrates a vitreous cutter system comprising the vitreous cutter sleeve of FIG. 6 and a vitreous cutter disposed in the vitreous cutter sleeve, according to one embodiment of the present invention.

As depicted in FIGS. 6 and 7, the first end 32a of the elongate tubular body 32 of the vitreous cutter sleeve 30 comprises a flared end portion (i.e., a bell-shaped end portion) configured to prevent the vitreous cutter sleeve 30 from entering too deep into the eye. That is, the peripheral flange of the flared end portion of the elongate tubular body 32 prevents the over-insertion of the vitreous cutter sleeve 30 into the eye. Obviously, the over-insertion of the sleeve 30 into the eye of the patient could pose a substantial safety risk to the patient. For example, without the flared end portion thereon, the first end 32a of the vitreous cutter sleeve 30 could potentially pass completely through its insertion hole in the eye, and possibly become lodged inside the eye of the patient.

Figure 13:
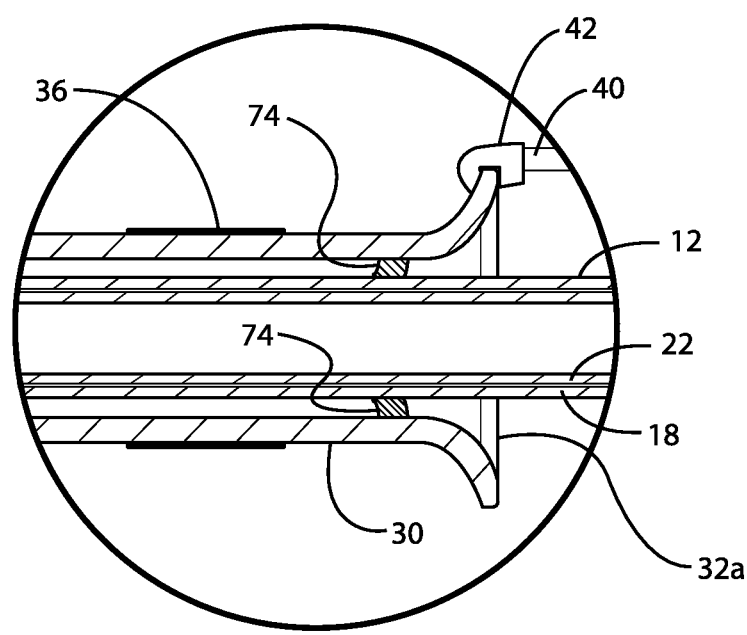
FIG. 13 is an enlarged view of the entrance to the internal passageway of the vitreous cutter sleeve in FIG. 9 to better illustrate the pierceable membrane disposed between the vitreous cutter and the vitreous cutter sleeve that maintains a generally liquid-tight seal between the cutter and the sleeve (Detail "B").

Turning again to FIGS. 6 and 7, it can be seen that the vitreous cutter sleeve 30 further includes a pierceable membrane 74 disposed within the central passageway 33 of the elongate tubular body 32 proximate to the first end 32a thereof. The pierceable membrane 74 near the entrance of the elongate tubular body 32 of the sleeve 30 is configured to create a substantially liquid-tight seal between an outer peripheral surface of the vitreous cutter and an inner peripheral surface of the peripheral sidewall of the vitreous cutter sleeve 30 after the vitreous cutter has penetrated the pierceable membrane 74 (e.g., see FIGS. 9 and 13). In an exemplary embodiment, the pierceable membrane 74 may be formed from a flexible, pierceable material, such as silicone or another suitable polymeric material or plastic. During the use of the vitreous cutter system, when the vitreous cutter is first inserted into the central cylindrical passageway 33 of the sleeve 30, an application of an axial force to the proximal end of the vitreous cutter by a user results in the piercing of the pierceable membrane 74 by the tip 16 of the vitreous cutter. After the pierceable membrane 74 has been pierced by the tip 16 of the vitreous cutter, the pierceable membrane 74 makes a generally liquid-tight seal so as to prevent intraocular fluid, cells, tissue, etc. from escaping from the first end 32a of the sleeve 30, and passing outside of the sleeve 30 over the surgical field. Advantageously, the generally liquid-tight seal formed by the pierceable membrane 74 prevents the spreading of biological tissue and cells outside the eye (e.g., malignant cells, etc.). Also, the sleeve 30 may be of a disposable type when used for the vitreous of a tumor biopsy.

While it is preferable to provide the pierceable membrane 74 near the entrance of the vitreous cutter sleeve 30 at the first end 32a thereof, it is possible for the pierceable membrane to be located at other positions within the central cylindrical passageway 33 of the sleeve 30. For example, as illustrated in FIG. 7, a pierceable membrane 76 alternatively may be provided proximate to the second end 32b of the vitreous cutter sleeve 30. The pierceable membrane 76 has the same construction as the pierceable membrane 74 described above, and performs in the same manner as the pierceable membrane 74. In still another embodiment, the vitreous cutter sleeve 30 may be provided with a plurality of pierceable membranes disposed in its central cylindrical passageway 33 for additional liquid-tight protection (e.g., the pierceable membrane 74 near the entrance of the sleeve 30 and the pierceable membrane 76 near the exit of the sleeve 30).

In FIGS. 6 and 7, it can be seen that the second end 32b of the elongate tubular body 32 of the vitreous cutter sleeve 30 comprises a pointed tip 34 configured to cut through tissue of the eye. That is, when the sleeve 30 is first inserted into the eye, the pointed tip 34 of sleeve 30 readily pierces the outer layer of the eye (i.e., the sclera of the eye) so that the sleeve 30 can be easily placed in the vitreous cavity of the eye. In the illustrative embodiment of FIG. 6, it can be seen that the pointed tip 34 of sleeve 30 has a generally tapered geometry with a side profile resembling that of a fountain pen tip.

With reference again to FIGS. 6 and 7, it can be seen that the elongate tubular body 32 of the vitreous cutter sleeve 30 comprises a plurality of opaque band portions 36 spaced apart along a length thereof. Each of the plurality of opaque bands portions 36 are spaced apart from one another by a respective one of a plurality of transparent band portions 38 (i.e., an alternating pattern of opaque bands portions 36 and transparent band portions 38 are disposed along the length of the elongate tubular body 32 of the sleeve 30). Each of the plurality of transparent band portions 38 are transparent to visible light so that visible light 44 may be transmitted through the sidewall of the sleeve (e.g., as diagrammatically shown in FIGS. 7 and 9 for several representative transparent band portions 38 near the second end 32b of the body 32). In the illustrative embodiment, each of the plurality of opaque band portions 36 are spaced apart from one another by a substantially constant distance such that the plurality of opaque bands portions 36 and the plurality of transparent band portions 38 are capable of being used to determine a depth of insertion of the vitreous cutter sleeve 30 into tissue of an eye. In the illustrative embodiment, the plurality of opaque band portions 36 of the elongate tubular body 32 of the sleeve 30 are formed by coating the peripheral sidewall of the elongate tubular body 32 with a thin layer of black material (e.g., as was described above for the vitreous cutter), while the transparent band portions 38 of the elongate tubular body 32 of the sleeve 30 are merely formed by exposed sections of the elongate tubular body 32 that is formed from a light-transmitting material, as will be described in more detail hereinafter.

Advantageously, the illuminated vitreous cutter sleeve 30 with the alternating opaque and transparent band portions 36, 38 allows the distance from the tip 34 of the sleeve 30 to be easily determined by a user thereof (e.g., by a retinal surgeon using the illuminated sleeve 30). Because light only shines through the transparent band portions 38 of the sleeve body 32, the user of the sleeve 30 can determine how many transparent band portions 38 of the sleeve 30 are covered up by the tissue in which it is embedded (e.g., tumor tissue). Because the transparent band portions 38 are spaced a generally constant, predetermined distance apart from one another by the opaque band portions 36 (e.g., a spacing distance of 1 to 2 millimeters), the quantity of transparent band portions 38 that are covered up by the tissue is indicative of the depth of insertion into the tissue (e.g., if one transparent band portion 38 is covered up by the tissue such that no that light is visible to the user passing through the covered transparent band portion 38, the insertion depth of the sleeve 30 may be 3.0 millimeters, which may correspond to the depth of the tissue being measured, such as the depth of a tumor).

Next, referring to FIG. 12, a second illustrative embodiment of a vitreous cutter sleeve 30' will be described. Referring to this figure, it can be seen that, in many respects, the second illustrative embodiment is similar to that of the first embodiment. Moreover, many elements are common to both such embodiments. For the sake of brevity, the elements that the second embodiment of the vitreous cutter sleeve has in common with the first embodiment will not be discussed because these components have already been explained in detail above. Furthermore, in the interest of clarity, these elements are denoted using the same reference characters that were used in the first embodiment.

Figure 12:
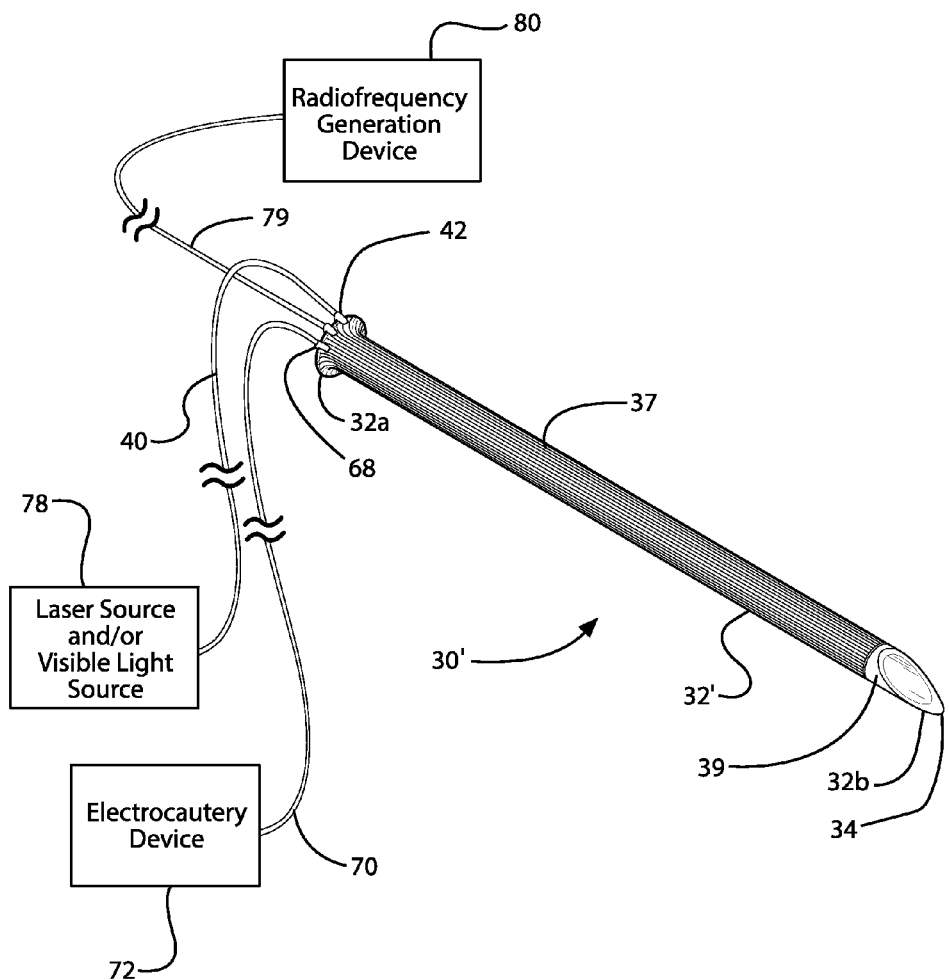
FIG. 12 illustrates an alternative vitreous cutter sleeve, according to another embodiment of the present invention, wherein the body of the vitreous cutter sleeve is provided with a continuous coating and/or insulation, expect for the tip of the vitreous cutter sleeve which remains exposed without a coating and/or insulation thereon.

In the second illustrative embodiment of FIG. 12, the elongate tubular body 32' of the vitreous cutter sleeve 30' comprises an opaque coating 37 (e.g., a thin layer of black material) from the first, flared end 32a of the body 32' to a transparent tip portion 39 at the second end 32b of the body 32' so as to enable the transparent tip portion 39 to function as a localized light source. Thus, rather than being provided with the alternating opaque and transparent band portions 36, 38 as the sleeve 30 of the embodiment of FIGS. 6 and 7, the body 32' of the vitreous cutter sleeve 30' in FIG. 12 has a continuous coating from its first end 32a to the exposed tip portion 39 proximate to its second end 32b. In addition to the coating 37 being opaque, the coating 37 may serve as an insulator in the illustrated embodiment of FIG. 12 so as to enable the exposed tip portion 39 to function as a localized cauterizer (as will be described in more detail hereinafter). Alternatively, the elongate tubular body 32' of the sleeve 30' may comprise a separate layer of insulation from the first end 32a to the exposed tip portion 39 at the second end 32b (e.g., a layer of insulation disposed underneath the opaque coating 37).

In addition, as shown in FIG. 12, the vitreous cutter sleeve 30' may comprise any one or all of the following devices operatively coupled to the elongate tubular body 32' thereof: (i) a laser source and/or visible light source 78 for generating from blue to infrared light, (ii) a radiofrequency generation device 80 for generating radiofrequency radiation, and (iii) an electrocautery device 72 for generating an electrical current that is capable of cauterizing tissue of the eye. Specifically, referring to FIG. 12, it can be seen that the laser source and/or visible light source 78 may be operatively connected to the body 32' of the sleeve 30' by means of the fiber optic 40. In the illustrative embodiment, the laser source and/or visible light source 78 is capable of generating electromagnetic radiation ranging from blue visible light to infrared radiation, and all wavelengths of radiation between blue visible light and infrared radiation. Also, in FIG. 12, it can be seen that the radiofrequency generation device 80 may be operatively connected to the body 32' of the sleeve 30' by means of the connecting wire 79 so that a radiofrequency current may be delivered to tissue at the location of the exposed tip portion 39 of the sleeve 30' inside the eye of the patient. In addition as shown in FIG. 12, the electrocautery device 72 may be operatively connected to the body 32' of the sleeve 30' by means of an electrically conductive wire 70 and a clip or connector 68 that electrically couples the wire 70 to the sleeve body 32'. As such, an electrical current that is generated by the electrocautery device 72 is capable of being transmitted through the conductive wire 70 and connector 68 so that it may be transmitted to the tissue of the eye by the electrically conductive material forming the sleeve 30' (as will be described hereinafter). Advantageously, when operatively coupled to the electrocautery device 72, the vitreous cutter sleeve 30' is capable of simultaneously cauterizing and penetrating a vascularized tissue of the eye. Similarly, when operatively coupled to the laser source 78, the vitreous cutter sleeve 30' is capable of coagulating vessels in the eye to stop any bleeding from the vessels. This is particular important if the sleeve 30' is being used to penetrate a tissue that is heavily vascularized and can readily bleed, such as the retina and the choroid of the eye.

Similar to the vitreous cutter 12 described above, the bodies 32, 32' of the vitreous cutter sleeves 30, 30' may be formed from a material is transparent to visible light from 400-800 nanometers (nm). The material forming the bodies 32, 32' of the vitreous cutter sleeves 30, 30' may also conduct infrared radiation, radiofrequency radiation, and/or an entire spectrum range of electromagnetic radiation ranging from visible blue light to infrared radiation. In addition, the material forming the bodies 32, 32' of the vitreous cutter sleeves 30, 30' may also be electrically conductive so as to transmit an electrical current therethrough. In the illustrative embodiment, the material forming the body 32 of the vitreous cutter sleeve 30, or the body 32' of the vitreous cutter sleeve 30', may comprise one of: (i) metal glass, (ii) amorphous glass, (iii) palladium alloy, (iv) zirconium alloy, and (v) aluminum nitryloxyde. Advantageously, the use of a composite material, such as a metal glass, for the bodies 32, 32' of the vitreous cutter sleeves 30, 30' allows the bodies 32, 32' of the sleeves 30, 30' to conduct electricity as well as light. Therefore, the vitreous cutter sleeves 30, 30' may transmit electricity through the bodies 32, 32' thereof so that they can function as cauterizers (i.e., when connected to electrocautery device 72 of FIG. 12). Also, advantageously, the use of a composite material, such as a metal glass, allows the bodies 32, 32' of the sleeves 30, 30' to transmit not only light and electricity, but also infrared radiation and radiofrequency radiation.

Figure 9:
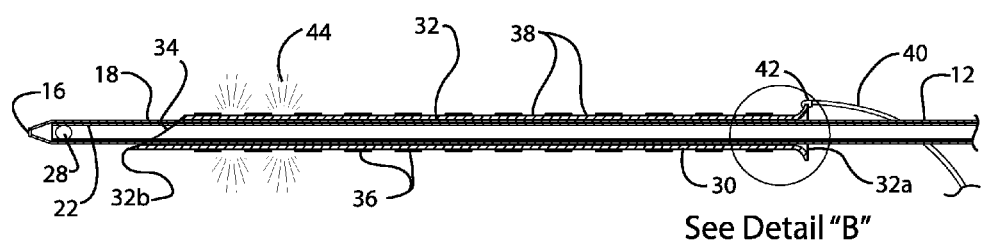
FIG. 9 is a longitudinal sectional view of the vitreous cutter system of FIG. 8, wherein the section is generally cut along the cutting-plane line B-B in FIG. 8.

Next, with reference to FIGS. 8 and 9, a vitreous cutter system comprising the vitreous cutter sleeve 30 described above and a vitreous cutter instrument 12 will be explained. As shown in these figures, the central cylindrical passageway 33 of the elongate tubular body 32 of the vitreous cutter sleeve 30 receives the vitreous cutter 12 therein. The vitreous cutter 12 generally includes an elongate outer tube 18 and an oscillating elongate inner tube 22 slidingly disposed in the elongate outer tube 18. In FIGS. 8 and 9, it can be seen that the elongate outer tube has a body 18 with a closed end tip 16. The body 18 of the elongate outer tube includes a sidewall extending in axial direction from the closed end tip 16, and the body 18 of the elongate outer tube defines a linear passageway closed at a distal end by the closed end tip 16. The elongate outer tube further includes an opening or aperture 28 disposed in the sidewall of the body 18. The opening 28 is disposed proximate to the closed end tip 16 of the body 18, and the opening 28 is configured to enable cutting of vitreous or tissue. Referring to the longitudinal sectional view of FIG. 9, it can be seen that the elongate inner tube 22 of the vitreous cutter 12 is arranged generally concentrically within the elongate outer tube. The elongate inner tube 22 is configured to oscillate back-and-forth within the elongate outer tube so as to be capable of cutting the vitreous or the tissue that enters the opening 28 in the body 18 of the elongate outer tube.

In the vitreous cutter system of FIGS. 8 and 9, the elongate inner tube 22 of the vitreous cutter 12 is configured to remove the cut vitreous or the cut tissue by the vitreous cutter 12 applying an aspiration force to the cut vitreous or the cut tissue. That is, the vitreous cutter 12 includes a vacuum source or vacuum pump 82 that is fluidly coupled to the passageway of the elongate inner tube 22 via fluid line 81 (see FIG. 8) so that cut vitreous or cut tissue is capable of being suctioned from the passageway of the elongate inner tube 22 after being cut thereby. In particular, the aspiration force applied by the vacuum pump 82 of the vitreous cutter 12 is configured to draw the cut vitreous or the cut tissue through the opening 28 disposed in the sidewall of the body 18 of the elongate outer tube.

In the vitreous cutter system of FIGS. 8 and 9, the vitreous cutter sleeve 30 is configured to contain the closed end tip 16 of the vitreous cutter 12 when the vitreous cutter 12 is being removed from the eye so as to prevent the closed end tip 16 from contacting and contaminating healthy tissue in the eye. That is, one advantage of the combination vitreous cutter 12 and sleeve 30 is that both instruments can be removed from the eye as a one-piece unit to prevent contamination resulting from the tip 16 of the vitreous cutter 12. Another advantage of the combination vitreous cutter 12 and sleeve 30 is that both instruments also can be inserted into the eye as a one-piece unit. When inserted as a one-piece unit into the eye, the combination vitreous cutter 12 and sleeve 30 is capable of passing through the conjunctiva, sclera, etc. without the need for an incision beforehand and the subsequent separate insertion of the cutter 12 into the incision. In one or more embodiments, the combination vitreous cutter 12 and sleeve 30 may be preassembled as a one-piece unit so as to maximize ease of use and sterility.

While the vitreous cutter sleeve 30 is described above in conjunction with the vitreous cutter system, it is to be understood that the vitreous cutter sleeve 30' may alternatively be used in conjunction with the vitreous cutter 12 of the vitreous cutter system. The selection of the particular one of the vitreous cutter sleeves 30, 30' that is used in the vitreous cutter system will depend on the particular medical/surgical procedure(s) that is being performed, and the steps that are involved in that procedure.

Now, referring to FIGS. 10 and 11, an exemplary manner in which the combination vitreous cutter 12 and sleeve 30 are used to remove tumor tissue from an eye 50 of a patient will be explained. Initially, the vitreous cutter 12 and sleeve 30 are inserted as single unit through the sclera 56 and conjunctiva of the eye 50, and into the vitreous cavity 60 of the eye 50 until the tip 34 of the sleeve 30 reaches a location that is proximate to a tumor 66 located in a posterior portion of the eye 50. When the vitreous cutter 12 and the vitreous cutter sleeve 30 are inserted as a single unit into the eye 50, the sharp tip 34 of the sleeve 30 is used to penetrate the outer layers of the eye 50, namely the conjunctiva, sclera, etc. Also, in the illustrative embodiment, when the cutter 12 and the vitreous cutter sleeve 30 are inserted into the eye 50, the tip 16 of the vitreous cutter 12 is recessed within the cylindrical cavity 33 of the sleeve 30 such that the sharp tip 34 of the sleeve 30 penetrates through the outer layers of the eye 50, and not the tip 16 of the vitreous cutter 12. In the illustrative embodiment of FIGS. 10 and 11, it can be seen that the unit comprising the cutter 12 and the sleeve 30 are inserted into the eye 50 at location that is disposed behind the anterior portion of the eye 50 (i.e., at a location behind the cornea 52 and the lens 54 of the eye 50). When inserted into the eye 50, the tip 34 of the vitreous cutter sleeve 30 is disposed proximate to the posterior portion of the eye (i.e., at a location proximate to the retina 58, arteries 62, and optic nerve 64 of the eye).

Figure 10:
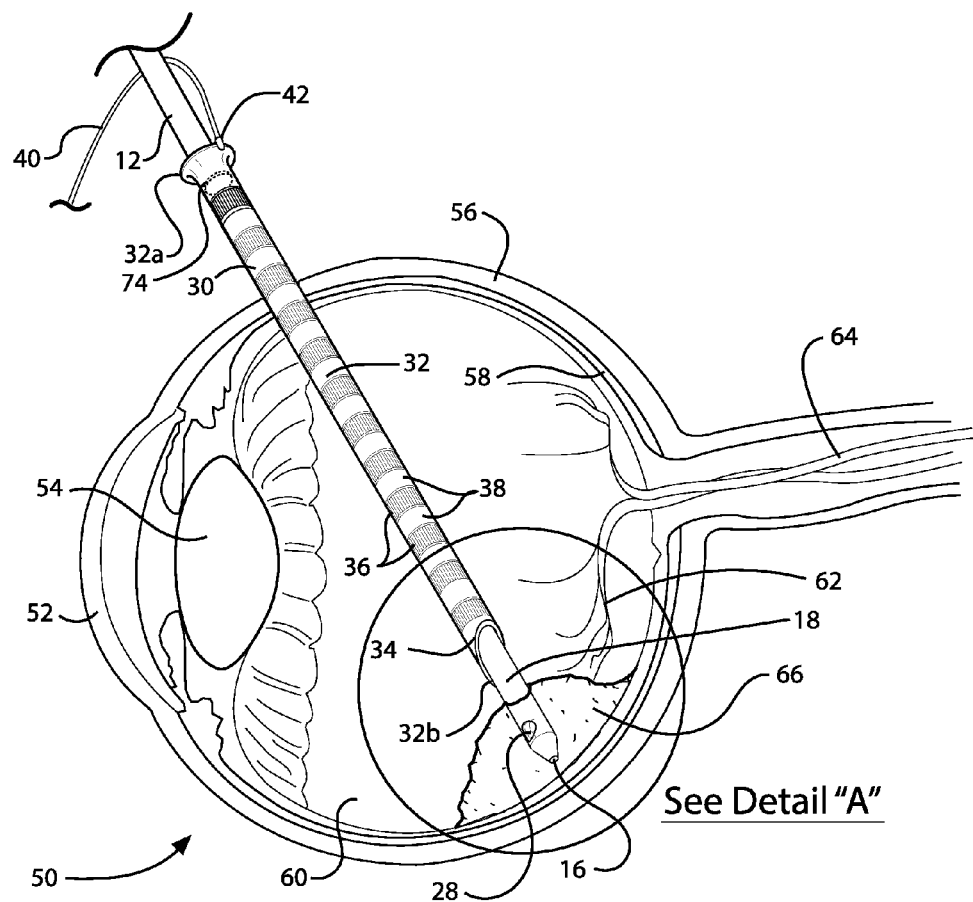
FIG. 10 illustrates the vitreous cutter system of FIG. 8 being used in the eye of a patient to remove tissue of a tumor, according to one embodiment of the present invention.
Figure 11:
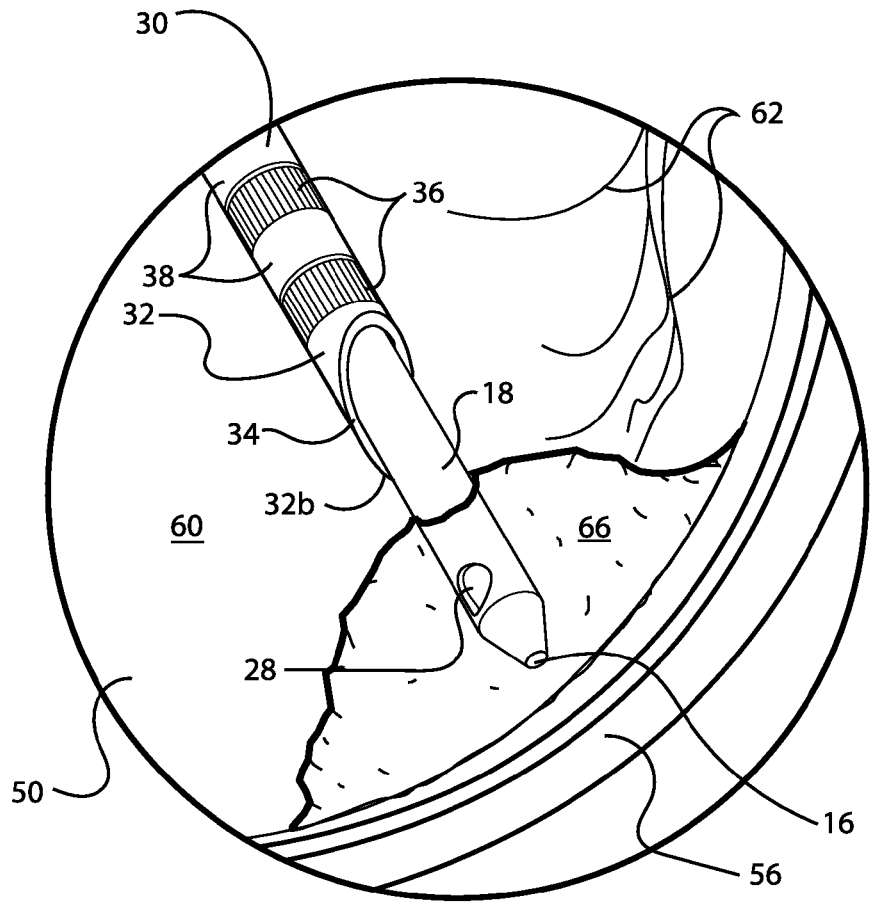
FIG. 11 is an enlarged view of the tip of the vitreous cutter and the tip of the vitreous cutter sleeve in FIG. 10 to better illustrate the manner in which the vitreous cutter is used to remove the tissue of the tumor (Detail "A")

Next, after the unit comprising the cutter 12 and the sleeve 30 has been inserted into the eye 50, the tip 16 of the vitreous cutter 12 is displaced out of the tip 34 of the vitreous cutter sleeve 30 until it reaches the position illustrated in FIGS. 10 and 11 where the tip 16 of the cutter 12 is embedded in the tumor 66. The cutter 12 is displaced out of the tip 34 of the sleeve 30 by the user applying a generally axial force against the proximal end portion of the cutter 12 so that it is slidingly displaced relative to the sleeve 30 until reaching the position of FIGS. 10 and 11 wherein it has penetrated the interior of the tumor 66. Once in position, the vitreous cutter 12 is used to remove the tissue of the tumor 66. In particular, tumor tissue that enters the cutter 12 through the opening 28 in the outer tube thereof is cut by the oscillating inner cutting tube 22 of the cutter 12. After which, the cut tissue of the tumor 66 is removed from the oscillating inner cutting tube 22 of the cutter 12 by the aspiration force that is generated by vacuum source/pump 82 that is fluidly coupled to the cutter inner tube 22. Once all of the tumor tissue has been removed, or at least substantially removed from the eye 50 of the patient, the tip 16 of the cutter 12 is retracted back into the sleeve 30 so that the tip 16 of the cutter 12 is completely contained within the cylindrical passageway 33 of the sleeve 30, and thus not exposed to the vitreous cavity 60 and the healthy tissue of the eye 50 of the patient. As such, the tip 16 of the cutter 12, which contacted the tissue of the tumor 66, is not able to contact and contaminate the vitreous cavity 60 and the healthy tissue of the eye 50. With the tip 16 of the cutter 12 in its retracted position within the sleeve 30, the vitreous cutter 12 and sleeve 30 are removed as a single unit from the eye 50, thereby minimizing any contamination by preventing the tip 16 of the cutter 12 from coming into contact with the eye 50 during the removal process. The cutter 12 and the sleeve 30 may also be used in a biopsy procedure where only a sample portion of the tumor tissue is removed, rather than the entire tumor 66. In the biopsy procedure, all of the other steps would be the same as that described above.

Advantageously, when the cutter 12 is removed from the eye 50 in the surgical procedure described above, the sleeve 30 houses the tip 16 of the cutter 12 therein so that any tumor cells contained thereon do not contaminate the wound by being left behind in the eye 50. If the tumor 66 is malignant, any tumor cells left behind by the cutter 12 can grow in another area of the eye 50. The containment of the tip 16 of the cutter 12 in the sleeve 30 prevents this dangerous spreading of tumor cells in the eye 50. Also, during the procedure, the sleeve 30 is advantageously able to be brought close to the tumor surface without actually penetrating the tumor surface (see FIGS. 10 and 11). Then, after the cutter 12 is retracted inside the sleeve 30, the cutter 12 can be simultaneously removed from the eye 50 with the sleeve 30 so as to not contaminate the exit wound. In addition, the sharp edges of the needle-like tip 34 of the sleeve 30 also may be used to advantageously to the cut the retina for gaining access to choroidal tumors, thereby creating a path for the generally blunt tip 16 of the cutter 12.

While the vitreous cutter sleeve 30 is described above in conjunction with the procedure for removing tumor tissue from the eye 50 of the patient, it is to be understood that the vitreous cutter sleeve 30' may alternatively be used in conjunction with this surgical procedure. The selection of the particular one of the vitreous cutter sleeves 30, 30' that is used in the surgical procedure will depend on the requisite steps of the procedure.

In addition to being used with the vitreous cutter 12 in the applications explained above, it is to be understood that the sleeves 30, 30' described herein may also be used in other medical applications, such as in medical imaging applications with various visualization devices. For example, the sleeves 30, 30' described herein may also be used with an endoscope, laser imaging probe, an optical coherence tomography (OCT) probe, a multiphoton probe, etc. These imaging probes may be contained within the cylindrical passageway 33 of the sleeve 30 in the same manner that the vitreous cutter 12 is contained therein. As such, these visualization devices may be used in conjunction with the sleeve 30 to image various portions of the eye or another portion of the body of the patient so as to determine surface geometries, thicknesses of body structures, etc. In addition, it is to be understood that the sleeves 30, 30' may also be used in conjunction with a laser coagulation probe so that the blood vessels or arteries within the eye (e.g., the blood vessels or arteries 62 in the eye 50 of FIGS. 10 and 11) may be coagulated during a surgical procedure being performed on the eye. In another suitable application, the sleeves 30, 30' described herein may be used in conjunction with an infusion tube inserted into the cylindrical passageway 33 of the sleeve 30, 30'. In this application, the pierceable membrane 74, 76 inside the cylindrical passageway 33 of the sleeve 30, 30' operates as a fluid lock to prevent the escaping of fluids from the sleeve 30, 30'.

Any of the features or attributes of the above described embodiments and variations can be used in combination with any of the other features and attributes of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A vitreous cutter sleeve, comprising:
an elongate tubular body having a first end and a second end disposed opposite to said first end, said elongate tubular body including a peripheral sidewall and a central passageway disposed through said elongate tubular body, said central passageway of said elongate tubular body configured to receive a vitreous cutter therein, at least a portion of said elongate tubular body being formed from a material that is transparent to visible light and electrically conductive, said material being further configured to conduct at least one of infrared radiation and radiofrequency radiation; and
an illumination device operatively coupled to said peripheral sidewall at said first end of said elongate tubular body, said elongate tubular body configured to transmit light from said illumination device in an axial direction along a length of said elongate tubular body such that said illumination device is capable of providing illumination to an inside portion of an eye through at least a portion of said peripheral sidewall of said elongate tubular body, said illumination device being in the form of a fiber optic; and
wherein said first end of said elongate tubular body comprises a light-transmitting connector member for connecting said fiber optic to said elongate tubular body of said vitreous cutter sleeve so that light is capable of being transmitted from said fiber optic to an interior of said peripheral sidewall of said elongate tubular body, said light-transmitting connector member being disposed on a portion of said elongate tubular body that does not enter said eye.

2. The vitreous cutter sleeve according to claim 1, further comprising at least one of following devices operatively coupled to said vitreous cutter sleeve: (i) a laser generation device for generating electromagnetic radiation ranging from blue light to infrared radiation, inclusive, (ii) a radiofrequency generation device for generating radiofrequency radiation, and (iii) an electrocautery device for generating an electrical current that is capable of cauterizing tissue of said eye.

3. The vitreous cutter sleeve according to claim 1, wherein said first end of said elongate tubular body comprises a flared end portion configured to prevent said vitreous cutter sleeve from entering too deep into said eye, and wherein said vitreous cutter sleeve further includes a pierceable membrane disposed within said central passageway of said elongate tubular body proximate to said first end, said pierceable membrane configured to create a substantially liquid-tight seal between an outer peripheral surface of said vitreous cutter and an inner peripheral surface of said peripheral sidewall of said vitreous cutter sleeve after said vitreous cutter has penetrated said pierceable membrane.

4. The vitreous cutter sleeve according to claim 1, wherein said second end of said elongate tubular body comprises a pointed tip configured to cut through tissue of said eye.

5. The vitreous cutter sleeve according to claim 1, wherein said elongate tubular body comprises a plurality of opaque band portions spaced apart along a length thereof, each of said plurality of opaque bands portions being spaced apart from one another by a respective one of a plurality of transparent band portions, each of said plurality of transparent band portions being transparent to visible light.

6. The vitreous cutter sleeve according to claim 5, wherein each of said plurality of opaque band portions are spaced apart from one another by a substantially constant distance such that said plurality of opaque bands portions and said plurality of transparent band portions are capable of being used to determine a depth of insertion of said vitreous cutter sleeve into tissue of said eye.

7. The vitreous cutter sleeve according to claim 5, wherein said plurality of opaque band portions of said elongate tubular body are formed by coating said peripheral sidewall of said elongate tubular body with a black material.

8. The vitreous cutter sleeve according to claim 1, wherein said elongate tubular body comprises an opaque coating from said first end to an exposed tip at said second end so as to enable said exposed tip to function as a localized light source.

9. The vitreous cutter sleeve according to claim 1, wherein said material is transparent to visible light from 400-800 nm, and wherein said material comprises one of: (i) metal glass, (ii) amorphous glass, (iii) palladium alloy, (iv) zirconium alloy, and (v) aluminum nitryloxyde.

10. The vitreous cutter sleeve according to claim 1, wherein said elongate tubular body comprises insulation from said first end to an exposed tip at said second end so as to enable said exposed tip to function as a localized cauterizer.

11. A vitreous cutter sleeve, comprising:
an elongate tubular body having a first end and a second end disposed opposite to said first end, said elongate tubular body including a peripheral sidewall and a central passageway disposed through said elongate tubular body, said central passageway of said elongate tubular body configured to receive a vitreous cutter therein, at least a portion of said elongate tubular body being formed from a material that is transparent to visible light, said material being further configured to conduct at least one of infrared radiation, radiofrequency radiation, and an electrical current, said first end of said elongate tubular body comprising a flared end portion configured to prevent said vitreous cutter sleeve from entering too deep into said eye, and said second end of said elongate tubular body comprising a pointed tip formed with said elongate tubular body so as to be capable of transmitting said visible light, said pointed tip configured to cut through tissue of said eye; and
an illumination device operatively coupled to said peripheral sidewall at said first end of said elongate tubular body, said elongate tubular body configured to transmit light from said illumination device in an axial direction along a length of said elongate tubular body such that said illumination device is capable of providing illumination to an inside portion of an eye through at least a portion of said peripheral sidewall of said elongate tubular body, said illumination device being in the form of a fiber optic; and
wherein said first end of said elongate tubular body comprises a light-transmitting connector member for connecting said fiber optic to said elongate tubular body of said vitreous cutter sleeve so that light is capable of being transmitted from said fiber optic to an interior of said peripheral sidewall of said elongate tubular body, said light-transmitting connector member being disposed on a portion of said elongate tubular body that does not enter said eye.

12. The vitreous cutter sleeve according to claim 11, wherein said elongate tubular body comprises a plurality of opaque band portions spaced apart along a length thereof, each of said plurality of opaque bands portions being spaced apart from one another by a respective one of a plurality of transparent band portions, each of said plurality of transparent band portions being transparent to visible light.

13. The vitreous cutter sleeve according to claim 12, wherein each of said plurality of opaque band portions are spaced apart from one another by a substantially constant distance such that said plurality of opaque bands portions and said plurality of transparent band portions are capable of being used to determine a depth of insertion of said vitreous cutter sleeve into tissue of said eye.

14. The vitreous cutter sleeve according to claim 11, further comprising at least one of following devices operatively coupled to said vitreous cutter sleeve: (i) a laser generation device for generating electromagnetic radiation ranging from blue light to infrared radiation, inclusive, (ii) a radiofrequency generation device for generating radiofrequency radiation, and (iii) an electrocautery device for generating an electrical current that is capable of cauterizing tissue of said eye.

15. A vitreous cutter system, comprising:
a vitreous cutter that includes:
an elongate outer tube with a body having a closed end tip, said body of said elongate outer tube including a sidewall extending in axial direction from said closed end tip, said body of said elongate outer tube defining a linear passageway closed at a distal end by said closed end tip, said elongate outer tube further including an opening disposed in said sidewall of said body, said opening being disposed proximate to said closed end tip of said body, and said opening being configured to enable cutting of vitreous or tissue; and
an elongate inner tube arranged concentrically within said elongate outer tube, said elongate inner tube being configured to oscillate so as to be capable of cutting the vitreous or the tissue that enters said opening in said body of said elongate outer tube; and
a vitreous cutter sleeve that includes:
an elongate tubular body having a first end and a second end disposed opposite to said first end, said elongate tubular body including a peripheral sidewall and a central passageway disposed through said elongate tubular body, said central passageway of said elongate tubular body slidingly receiving said vitreous cutter therein, at least a portion of said elongate tubular body being formed from a material that is transparent to visible light and electrically conductive, said material being further configured to conduct at least one of infrared radiation and radiofrequency radiation, said first end of said elongate tubular body comprising a flared end portion configured to prevent said vitreous cutter sleeve from entering too deep into said eye, and said second end of said elongate tubular body comprising a pointed tip formed with said elongate tubular body so as to be capable of transmitting said visible light, said pointed tip configured to cut through tissue of said eye; and
an illumination device operatively coupled to said elongate tubular body such that said illumination device is capable of providing illumination to an inside portion of an eye through at least a portion of said peripheral sidewall of said elongate tubular body, said illumination device being in the form of a fiber optic; and wherein said first end of said elongate tubular body comprises a light-transmitting connector member for connecting said fiber optic to said elongate tubular body of said vitreous cutter sleeve so that light is capable of being transmitted from said fiber optic to an interior of said peripheral sidewall of said elongate tubular body, said light-transmitting connector member being disposed on a portion of said elongate tubular body that does not enter said eye.

16. The vitreous cutter system according to claim 15, wherein said elongate inner tube of said vitreous cutter is configured to remove the cut vitreous or the cut tissue by said vitreous cutter applying an aspiration force to the cut vitreous or the cut tissue.

17. The vitreous cutter system according to claim 16, wherein said aspiration force applied by said vitreous cutter is configured to draw the cut vitreous or the cut tissue through said opening disposed in said sidewall of said body of said elongate outer tube.

18. The vitreous cutter system according to claim 15, wherein said vitreous cutter sleeve is configured to contain said closed end tip of said vitreous cutter when said vitreous cutter is being removed from said eye so as to prevent said closed end tip from contacting and contaminating healthy tissue in said eye.

19. The vitreous cutter system according to claim 15, wherein said elongate tubular body comprises a plurality of opaque band portions spaced apart along a length thereof, each of said plurality of opaque bands portions being spaced apart from one another by a respective one of a plurality of transparent band portions, each of said plurality of transparent band portions being transparent to visible light; and wherein each of said plurality of opaque band portions are spaced apart from one another by a substantially constant distance such that said plurality of opaque bands portions and said plurality of transparent band portions are capable of being used to determine a depth of insertion of said vitreous cutter sleeve into tissue of said eye.

* * * * *